United States Patent [19]

Stack

[11] Patent Number: 4,948,509
[45] Date of Patent: Aug. 14, 1990

[54] ANAEROBIC FERMENTATION PROCESS

[75] Inventor: Charles R. Stack, Broken Arrow, Okla.

[73] Assignee: Charles Stack & Associates, Inc., Tulsa, Okla.

[21] Appl. No.: 236,514

[22] Filed: Aug. 24, 1988

[51] Int. Cl.$^5$ .............................................. C02F 3/28
[52] U.S. Cl. ................................... 210/603; 210/608; 210/612
[58] Field of Search ........ 210/603, 605, 608, 610–615, 210/623, 630, 707

[56] References Cited

U.S. PATENT DOCUMENTS

| | | | |
|---|---|---|---|
| 4,053,395 | 10/1977 | Switzgable | 210/605 X |
| 4,267,050 | 5/1981 | Conway et al. | 210/608 |
| 4,334,997 | 6/1982 | Peterson | 210/603 |
| 4,521,310 | 6/1985 | Casey | 210/603 |
| 4,780,207 | 10/1988 | Engwirda | 210/603 |

Primary Examiner—Tom Wyse
Attorney, Agent, or Firm—Laney, Dougherty, Hessin & Beavers

[57] ABSTRACT

An improved anaerobic fermentation process and apparatus for converting an influent liquid containing suspended organic matter to effluent gas and liquid products are provided. The influent liquid is introduced into and maintained in an anaerobic fermentation reactor containing anaerobic microorganisms at a temperature and a first pressure and for a time sufficient to form a gas containing methane and to form a liquid containing dissolved gas and suspended bacterial cell mass particles. The liquid is introduced into and maintained in a flotation vessel at a temperature, at a second pressure and for a time whereby gas dissolved in the liquid is liberated forming solution gas bubbles which rise and cause the suspended bacterial cell mass particles to be floated to the surface of the liquid. The floated bacterial cell mass particles are withdrawn from the surface of the liquid and from the flotation zone and recycled to the fermentation zone.

12 Claims, 1 Drawing Sheet

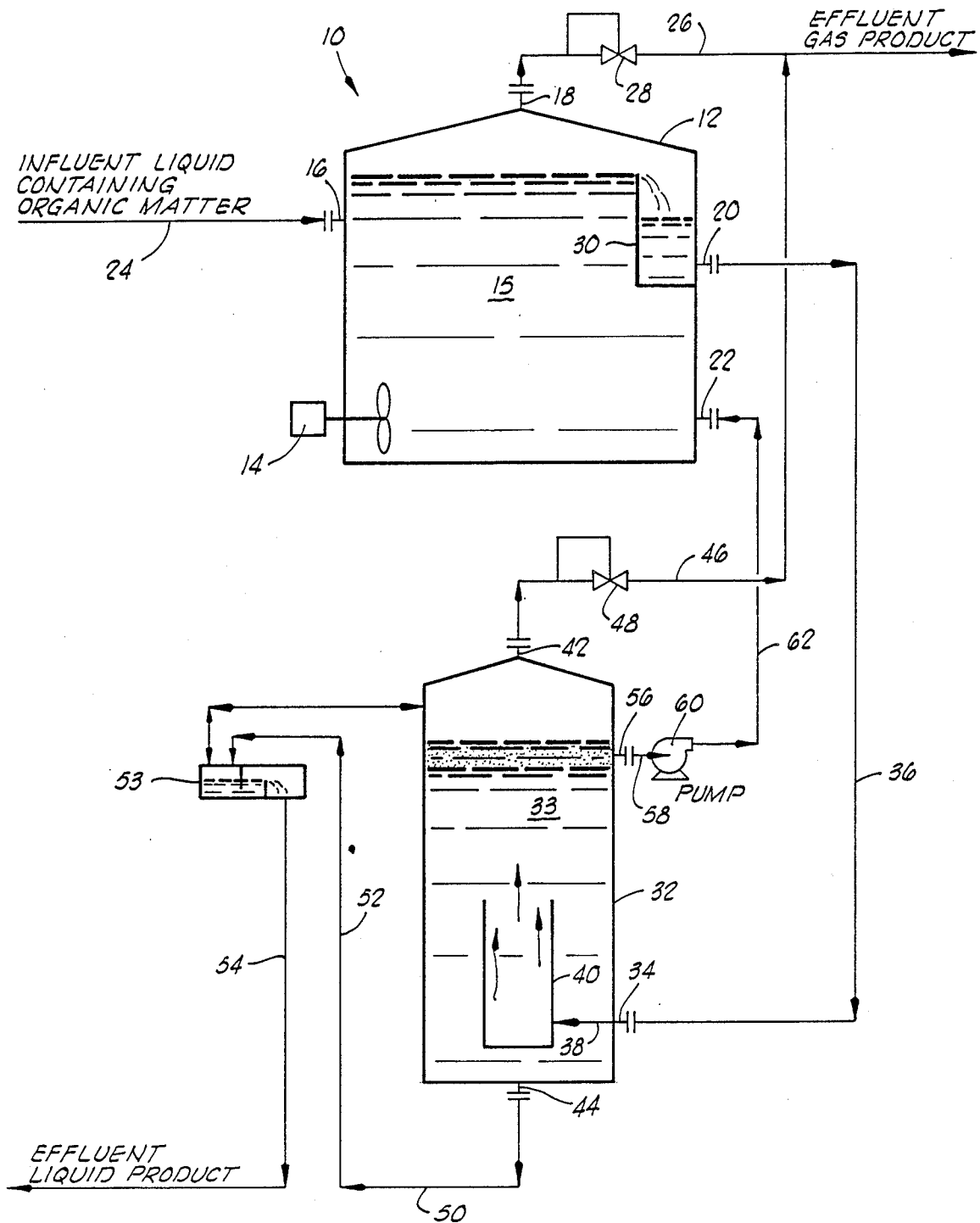

ANAEROBIC FERMENTATION PROCESS

BACKGROUND OF THE INVENTION

1. Field of the Invention

The present invention relates to an improved anaerobic fermentation process for converting an influent liquid containing suspended organic matter to effluent gas and liquid products.

2. Description of the Prior Art

By-product or liquid waste streams containing suspended organic matter have heretofore been anaerobicly fermented to produce a methane-containing gas and other desired products. For example, waste water effluents from food processing plants commonly contain suspended organic matter, have high oxygen demands and are not acceptable under environmental laws and regulations for disposition in lakes or rivers. Such waste water streams are often processed in anaerobic and/or aerobic fermentation systems to remove the organic constituents and purify the waste water to an environmentally acceptable level.

In a typical anaerobic fermentation process, influent liquid containing suspended organic matter is introduced into an anaerobic fermentation zone which excludes air or oxygen and contains anaerobic microorganisms for converting the suspended organic matter to fermentation products. The fermentation products are comprised of a gas containing carbon dioxide and methane which is separated and utilized as an energy or heat source, and depending upon the particular type of influent liquid and organic matter contained therein, other products such as alcohols, antibiotics and the like can be produced. The anaerobic fermentation reaction produces bacterial cell mass, commonly referred to as sludge, which is recirculated to the reactor vessel. The effluent liquid produced is substantially free of organic matter and suspended solids.

The separation and removal of gas and bacterial cell mass from the reacted liquid have heretofore been accomplished by separate degasification and solids settling steps. That is, the reacted liquid containing suspended bacterial cell mass particles is conducted from the anaerobic fermentation reactor to a settling tank wherein the bacterial cell mass particles are allowed to settle to the bottom of the tank. The settled particles are withdrawn from the tank and recycled to the reactor. Gas entrained in the reacted liquid makes the suspended bacterial cell mass particles difficult to settle. Therefore, a degasifier is generally employed between the reactor vessel and the settling tank.

By the present invention an improved anaerobic fermentation process and apparatus are provided which eliminate the degasification and settling steps and substitute a flotation step which more economically and efficiently accomplishes degasification and separation of bacterial cell mass particles.

SUMMARY OF THE INVENTION

An improved anaerobic fermentation process for converting an influent liquid containing suspended organic matter to effluent gas and liquid products is provided. The influent liquid is introduced into an anaerobic fermentation zone containing anaerobic microorganisms for converting the suspended organic matter into fermentation products including methane-containing gas and bacterial cell mass. The influent liquid is maintained in the fermentation zone at a temperature, at a first pressure and for a time sufficient to convert the organic matter to methane-containing gas and to form a reacted liquid containing dissolved gas and suspended bacterial cell mass particles. The liquid containing dissolved gas and suspended bacterial cell mass particles is withdrawn from the fermentation zone and introduced into a flotation zone. The liquid is maintained in the flotation zone at a temperature, at a second pressure and for a time whereby solution gas dissolved in the liquid is liberated therefrom forming bubbles which rise and cause the suspended bacterial cell mass particles to be floated to the surface of the liquid. The bacterial cell mass particles are withdrawn from the surface of the liquid and from the flotation zone and recycled to the fermentation zone. The effluent liquid is conducted from the flotation zone to a point of further processing or use. Apparatus for carrying out the improved process is also provided.

It is, therefore, a general object of the present invention to provide an improved anaerobic fermentation process and apparatus.

A further object of the present invention is the provision of an improved anaerobic fermentation process which substitutes a single flotation step for the degasification and settling steps heretofore utilized.

A further object of the present invention is the provision of an improved anaerobic fermentation process and apparatus wherein the quantity of bacterial cell mass recycled to the fermentation reactor is maximized and the effluent liquid produced is of high purity with a low concentration of suspended solids therein.

Other and further objects, features and advantages of the present invention will be readily apparent to those skilled in the art upon a reading of the description of preferred embodiments which follows when taken in conjunction with the accompanying drawing.

BRIEF DESCRIPTION OF THE DRAWING

In the drawing forming a part of this disclosure, apparatus for carrying out the improved anaerobic fermentation process is illustrated schematically.

DESCRIPTION OF PREFERRED EMBODIMENTS

Referring now to the drawing, apparatus of this invention is illustrated and generally designated by the numeral 10. The apparatus 10 is comprised of an anaerobic fermentation reactor 12 which includes an externally driven paddle-type stirrer 14, or the equivalent. The reactor 12 includes an inlet connection 16 for the introduction of influent liquid containing organic matter, an effluent gas outlet connection 18, a reacted liquid outlet connection 20 and a bacterial cell mass slurry inlet connection 22.

A conduit 24 is connected to the inlet connection 16 of the reactor 12 for conducting an influent liquid stream from a source thereof to the reactor 12. A conduit 26 connects the effluent gas outlet connection 18 to a point of further gas processing or use, and a backpressure controller 28 is disposed in the conduit 26. An overflow weir box 30 is provided within the reactor 12 connected over the reacted liquid outlet connection 20. The weir box 30 functions to maintain a constant level of liquid within the reactor 12 regardless of the flow rate of influent liquid thereinto.

A flotation vessel 32 is provided which includes a liquid inlet connection 34 near the bottom thereof. A conduit 36 is connected between the reacted liquid outlet connection 20 of the reactor 12 and the liquid inlet connection 34 of the flotation vessel 32. The liquid inlet connection 34 is internally connected by a conduit 38 to a vertical riser 40 disposed within the vessel 32. A gas outlet connection 42 is provided at the top of the flotation vessel 32, and an effluent liquid outlet connection 44 is provided at the bottom of the vessel 32. A conduit 46 is connected to the gas outlet connection 42 and to the conduit 26, and a backpressure controller 48 is disposed in the conduit 46.

A conduit 50 is connected to the effluent liquid outlet connection 44 of the flotation vessel 32 which conducts the effluent liquid to a standpipe 52 for controlling the liquid level within the vessel 32. The standpipe 52 is connected to a pressure equalized weir box, generally designated by the numeral 53, which is in turn connected to a conduit 54. The conduit 54 conducts the effluent liquid to a point of further processing or use. The level controlling standpipe 52 maintains a liquid level within the vessel 32 which is independent of the flow rate of reacted liquid introduced thereinto. A floated particle slurry outlet connection 56 is provided in the flotation vessel 32 at a point just below the liquid level maintained by the standpipe 52. A conduit 58 connects the outlet connection 56 to a slurry pump 60. The discharge of the pump 60 is connected by a conduit 62 to the inlet connection 22 of the reactor 12.

In operation of the apparatus 10, influent liquid containing suspended organic matter is conducted to the reactor 12 by way of the conduit 24. A body of influent liquid 15 is produced within the reactor 12 having a level maintained by the spillover weir box 30, and methane gas producing microorganisms are introduced into the liquid body 15. The paddle stirrer 14 continuously circulates the liquid, suspended organic matter and microorganisms within the liquid body 15, and the organic matter is anaerobicly fermented by the microorganisms whereby it is converted to fermentation products including methane-containing gas and bacterial cell mass.

The reactor 12 is of a size such that the methane-containing gas not dissolved in the reacted liquid separates from the liquid body 15 and is withdrawn from the reactor 12 by way of the outlet connection 18 and the conduit 26 connected thereto. The pressure controller 28 maintains the pressure within the reactor 12 at a first pressure, preferably in the range of from about 8 inches to about 20 inches of water column above atmospheric pressure. The influent liquid introduced into the reactor 12 is preferably at a temperature in the range of from about 80° F. to about 130° F.

The reacted liquid which spills over the weir box 30 and is withdrawn from the reactor 12 by way of the outlet connection 20 thereof contains dissolved gas and suspended bacterial cell mass particles. The reacted liquid flows by way of the conduit 36, the connection 34, the conduit 38 and the internal riser 40 into the flotation vessel 32. The riser 40 causes the liquid to flow upwardly towards the top portion of the flotation vessel 32.

The pressure controller 48 disposed in the gas conduit 46 maintains the pressure level within the flotation vessel 32 at a second pressure in the range of from about 0 inches to about 6 inches of water column. While a positive (above atmospheric) pressure is preferred, a negative pressure, i.e., a vacuum, can be maintained within the flotation vessel by means of a vacuum pump disposed in the conduit 46 (not shown) in lieu of the pressure controller 48. The temperature of the liquid within flotation vessel 32 is generally equal to or slightly less than the temperature of the liquid body 15 within the reactor 12, i.e., a temperature in the range of from about 80° F. to about 130° F.

A body 33 of reacted liquid containing dissolved gas and suspended bacterial cell mass particles is maintained within the flotation vessel 32 by the standpipe 52. The pressure differential between the reactor 12 and the flotation vessel 32 causes gas dissolved in the reacted liquid within the liquid body 33, i.e., solution gas, to be liberated therein. Such liberation of solution gas causes the formation of numerous gas bubbles within the liquid body 33 which attach themselves to bacterial cell mass particles and rise whereby the bacterial cell mass particles are floated to or near the surface of the liquid body 33 within the flotation vessel 32.

A slurry of floated bacterial cell mass particles is withdrawn from the flotation vessel 32 by way of the outlet 56, conduit 58 and slurry pump 60. From the discharge of the pump 60, the slurry is conducted by the conduit 62 and the inlet connection 22 back into the liquid body 15 within the reactor 12. If the pump 60 is operated continuously, or if it otherwise continues to operate when there is no influent liquid flowing into the reactor 12 and no reacted liquid flowing into the flotation vessel 32, the slurry pump 60 and associated conduits and the conduit 36 simply recirculate liquid between the reactor 12 and flotation vessel 32.

Solution gas formed in the flotation vessel 32 separates from the liquid body 33 therein, and is withdrawn therefrom by way of the outlet connection 42, the conduit 46 and the pressure controller 48. The conduit 46 conducts the solution gas to the conduit 26 whereby it is combined with the gas withdrawn from the reactor 12, and the combined stream is conducted to a point of further processing or use.

Effluent liquid which is substantially free of suspended organic matter and bacterial cell mass particles is withdrawn from the flotation vessel 32 by way of the outlet connection 44 and conduit 50 connected thereto. The conduit 50 conducts the effluent liquid to the standpipe 52, and the conduit 54 conducts the effluent liquid to a point of further processing or use.

Thus, in accordance with the improved process of the present invention, the reacted liquid from the anaerobic fermentation reactor 12 containing dissolved gas and suspended bacterial cell mass particles is conducted to the flotation vessel 32 rather than to a degasifier and then to a clarifier (settling tank). A pressure differential is maintained between the reactor 12 and flotation vessel 32 whereby solution gas breaks out of the reacted liquid within the flotation vessel 32 forming bubbles therein which float the bacterial cell mass particles to the surface of the reacted liquid body 33. The bacterial cell mass particles are continuously withdrawn from the flotation vessel 32 and returned to the reactor 12.

A variety of anaerobic microorganisms can be utilized for converting suspended organic matter to methane-containing gas and other products. When the influent liquid is waste water containing suspended organic matter such as the waste water streams produced by food processing plants, one or more bacteria selected from the group consisting of chemoheterotrophic nonmethanogens, acetogens and methanogens are preferably utilized. Such bacteria are more fully described in the article entitled "Anaerobic Biotechnology for Industrial Wastewater Treatment" by Richard E. Speece, *Environmental Science & Technology*, Vol. 17, No. 9, 1983. The microorganisms are initially charged to the reactor 12 by combining them with the influent liquid and are prevented from passing through the apparatus 10 by the flotation vessel 32, etc.

As will now be readily understood by those skilled in the art, the influent liquid containing suspended organic matter is maintained in the reactor 12 at a temperature, at a pressure and for a time sufficient to cause the organic matter to react with microorganisms therein and form anaerobic fermentation products including methane-containing gas and a reacted liquid containing dissolved gas and suspended bacterial cell mass particles. The reacted liquid is conducted to the flotation vessel 32 wherein it is maintained at a temperature, at a pressure and for a time such that solution gas is liberated which floats the bacterial cell mass particles to the liquid surface from where the bacterial cell mass particles are removed and recycled to the reactor 12.

In order to further illustrate the present invention, the following example is given.

EXAMPLE

A 70 gallons/minute stream of food processing plant waste water containing suspended and dissolved chemical oxygen demanding organic material in a concentration of about 10,000 ppm is conducted by the conduit 24 to the fermentation reactor 12. The reactor 12 has a volume of about 24,000 cubic feet, and contains a bacterial cell mass concentration of methanogen bacteria of about 0.08 pounds of cell mass/gallon of waste water. The temperature of the influent liquid is in the range of from about 95° F. to about 105° F., and a pressure of from about 8 inches to about 12 inches of water column is maintained on the reactor 12 by the pressure controller 28. 41.7 standard cubic feet/minute of gas comprised of about 60% by volume methane and the remainder carbon dioxide are withdrawn from the reactor 12 by way of the conduit 26. 70 gallons/minute of reacted liquid containing dissolved gas and suspended bacterial cell mass particles are conducted by the conduit 36 from the reactor 12 to the flotation vessel 32. The pressure maintained on the flotation vessel 32 by the pressure controller 48 is in the range of from about 0 inches to about 3 inches of water column. 4.0 standard cubic feet/minute of solution gas are withdrawn from the flotation tank 32 by way of the conduit 46 and combined with the gas withdrawn from the reactor 12. A 20 gallons/minute slurry of floated bacterial cell mass particles is continuously recycled from the flotation vessel 32 to the reactor 12 by way of the pump 60 and the conduit 62. The slurry of bacterial cell mass particles contains about 1.5% by weight bacterial cell mass with the remainder being water. 70 gallons/minute of effluent treated water at a temperature of about 93° F. are withdrawn from the flotation vessel 32 by way of the conduit 50, the standpipe 52 and the conduit 54.

Thus, the present invention is well adapted to carry out the objects and attain the ends and advantages mentioned as well as those inherent therein. While presently preferred embodiments have been described for purposes of this disclosure, numerous changes in the arrangement of method steps and apparatus parts can be made by those skilled in the art, which changes are encompassed within the spirit of this invention as defined by the appended claims.

What is claimed is:

1. An improved anaerobic fermentation process for converting an influent liquid containing suspended organic matter to effluent gas and liquid products comprising the steps of:
   introducing said influent liquid into an anaerobic fermentation zone containing anaerobic microorganisms for converting said suspended organic matter into fermentation products including a gas containing methane and bacterial cell mass particles;
   maintaining said influent liquid in said fermentation zone at a temperature, at a first pressure and for a time sufficient to form said gas and to form a liquid containing dissolved gas and suspended bacterial cell mass particles;
   withdrawing said liquid containing dissolved gas and suspended bacterial cell mass particles from said fermentation zone;
   introducing said liquid into a flotation zone;
   maintaining said liquid in said flotation zone at a temperature, at a second pressure and for a time whereby solution gas dissolved in said liquid is liberated therein forming bubbles which rise and cause said suspended bacterial cell mass particles to be floated to the surface of said liquid;
   withdrawing said bacterial cell mass particles from the surface of said liquid and from said flotation zone;
   recycling said withdrawn bacterial cell mass particles to said fermentation zone; and
   conducting the remaining liquid from said flotation zone to a point of further processing or use.

2. The process of claim 1 which is further characterized to include the steps of:
   withdrawing undissolved gas from said fermentation zone;
   withdrawing solution gas from said flotation zone;
   combining said withdrawn gas from said fermentation zone with said withdrawn gas from said flotation zone; and
   conducting the resultant combined gas to a point of further processing or use.

3. The process of claim 2 wherein said influent liquid containing suspended organic matter is waste water.

4. The process of claim 3 wherein said anaerobic microorganisms for converting said suspended organic matter in said fermentation zone are selected from the group consisting of chemoheterotrophic nonmethanogens, acetogens and methanogens.

5. The process of claim 4 wherein said fermentation zone is continuously stirred.

6. The process of claim 5 wherein said liquid in said fermentation zone and said liquid in said flotation zone are maintained at temperatures in the range of from about 80° F. to about 130° F.

7. The process of claim 6 wherein said first pressure is in the range of from about 8 inches of water column to about 20 inches of water column.

8. The process of claim 7 wherein said second pressure is in the range of from about 0 inches of water column to about 6 inches of water column.

9. An improved anaerobic fermentation process for converting influent waste water containing suspended organic matter to effluent gas and treated water comprising the steps of:
   introducing said waste water into an anaerobic fermentation zone containing anaerobic microorganisms for converting suspended organic matter in said waste water into a gas containing methane and bacterial cell mass;

maintaining said waste water in said fermentation zone at a temperature in the range of from about 80° F. to about 130° F. and at a first pressure in the range of from about 8 inches to about 20 inches of water column for a time sufficient to form said gas and to form water containing dissolved gas and suspended bacterial cell mass particles;

withdrawing undissolved gas from said fermentation zone;

withdrawing said water containing dissolved gas and suspended bacterial cell mass particles from said fermentation zone;

introducing said water into a flotation zone;

maintaining said water in said flotation zone at a temperature in the range of from about 80° F. to about 130° F. and at a second pressure in the range of from about 0 inches to about 6 inches of water column and for a time whereby solution gas dissolved in said water is liberated forming bubbles therein which rise and cause said suspended bacterial cell mass particles to be floated to the surface of said water;

withdrawing said bacterial cell mass particles from the surface of said water and from said flotation zone;

recycling said withdrawn bacterial cell mass particles to said fermentation zone;

withdrawing solution gas from said flotation zone;

conducting water from said flotation zone to a point of further processing or use;

combining said withdrawn gas from said fermentation zone with said withdrawn gas from said flotation zone; and conducting the resultant combined gas to a point of further processing or use.

10. The process of claim 9 wherein said anaerobic microorganisms are selected from the group consisting of chemoheterotrophic nonmethanogens, acetogens and methanogens.

11. The process of claim 10 wherein said first pressure is about 12 inches of water column.

12. The process of claim 11 wherein said second pressure is about 3 inches of water column.

* * * * *